(12) United States Patent
Rao

(10) Patent No.: US 8,128,687 B2
(45) Date of Patent: *Mar. 6, 2012

(54) DRUG-ELUTING STENT WITH FILAMENT STRANDS

(75) Inventor: K. T. Venkateswara Rao, San Jose, CA (US)

(73) Assignee: Advanced Cardiovascular Systems, Inc., Santa Clara, CA (US)

( * ) Notice: Subject to any disclaimer, the term of this patent is extended or adjusted under 35 U.S.C. 154(b) by 250 days.

This patent is subject to a terminal disclaimer.

(21) Appl. No.: 11/510,431

(22) Filed: Aug. 25, 2006

(65) Prior Publication Data

US 2006/0287709 A1     Dec. 21, 2006

Related U.S. Application Data

(62) Division of application No. 10/293,108, filed on Nov. 13, 2002, now Pat. No. 7,144,422.

(51) Int. Cl.
*A61F 2/06* (2006.01)
(52) U.S. Cl. .............. 623/1.42; 623/1.13; 623/1.15
(58) Field of Classification Search ........... 623/1.13, 623/1.22, 1.23, 1.38, 1.39, 1.42, 1.43
See application file for complete search history.

(56) References Cited

U.S. PATENT DOCUMENTS

| 3,839,743 A | 10/1974 | Schwarcz |
| 4,346,028 A | 8/1982 | Griffith |
| 4,377,030 A | 3/1983 | Pettenpaul et al. |
| 4,417,576 A | 11/1983 | Baran |
| 4,423,725 A | 1/1984 | Baran et al. |
| 4,633,873 A | 1/1987 | Dumican et al. |
| 4,656,083 A | 4/1987 | Hoffman et al. |
| 4,718,907 A | 1/1988 | Karwoski et al. |
| 4,722,335 A | 2/1988 | Vilasi |
| 4,723,549 A | 2/1988 | Wholey et al. |
| 4,732,152 A | 3/1988 | Wallsten et al. |
| 4,733,665 A | 3/1988 | Palmaz |
| 4,739,762 A | 4/1988 | Palmaz |
| 4,768,507 A | 9/1988 | Fischell et al. |

(Continued)

FOREIGN PATENT DOCUMENTS

DE    36 40 745    6/1987

(Continued)

OTHER PUBLICATIONS

Bull, "Parylene Coating for Medical Applications", Medical Product Manufacturing News, 2 pgs, Mar. 1993.

(Continued)

*Primary Examiner* — Bruce E Snow
(74) *Attorney, Agent, or Firm* — Squire Sanders (US) LLP

(57) ABSTRACT

An intravascular stent having a prefabricated, patterned polymeric sleeve for controlled release of therapeutic drugs and for delivery of the therapeutic drugs in localized drug therapy in a blood vessel is disclosed. The polymeric sleeve is attached to at least a portion of an outside surface area of the stent structure. Alternatively, a plurality of individual microfilament strands are longitudinally attached to an outer surface of a stent structure in a spaced apart orientation and loaded with at least one therapeutic drug for the release thereof at a treatment site. The stent has a high degree of flexibility in the longitudinal direction, yet has adequate vessel wall coverage and radial strength sufficient to hold open an artery or other body lumen. Methods for making the same are also disclosed.

8 Claims, 3 Drawing Sheets

U.S. PATENT DOCUMENTS

| | | |
|---|---|---|
| 4,776,337 A | 10/1988 | Palmaz |
| 4,816,339 A | 3/1989 | Tu et al. |
| 4,877,030 A | 10/1989 | Beck et al. |
| 4,878,906 A | 11/1989 | Lindemann et al. |
| 4,879,135 A | 11/1989 | Greco et al. |
| 4,902,289 A | 2/1990 | Yannas |
| 4,994,298 A | 2/1991 | Yasuda |
| 5,019,090 A | 5/1991 | Pinchuk |
| 5,059,211 A | 10/1991 | Stack et al. |
| 5,062,829 A | 11/1991 | Pryor et al. |
| 5,064,435 A | 11/1991 | Porter |
| 5,084,065 A | 1/1992 | Weldon et al. |
| 5,085,629 A | 2/1992 | Goldberg et al. |
| 5,100,429 A | 3/1992 | Sinofsky et al. |
| 5,108,370 A | 4/1992 | Walinsky |
| 5,108,755 A | 4/1992 | Daniels et al. |
| 5,123,917 A | 6/1992 | Lee |
| 5,151,105 A | 9/1992 | Kwan-Gett |
| 5,156,623 A | 10/1992 | Hakamatsuka et al. |
| 5,158,548 A | 10/1992 | Lau et al. |
| 5,163,951 A | 11/1992 | Pinchuk et al. |
| 5,163,952 A | 11/1992 | Froix |
| 5,163,958 A | 11/1992 | Pinchuk |
| 5,192,311 A | 3/1993 | King et al. |
| 5,197,977 A | 3/1993 | Hoffman, Jr. et al. |
| 5,199,951 A | 4/1993 | Spears |
| 5,234,456 A | 8/1993 | Silvestrini |
| 5,234,457 A | 8/1993 | Andersen |
| 5,236,447 A | 8/1993 | Kubo et al. |
| 5,279,594 A | 1/1994 | Jackson |
| 5,282,860 A | 2/1994 | Matsuno et al. |
| 5,289,831 A | 3/1994 | Bosley |
| 5,290,271 A | 3/1994 | Jernberg |
| 5,306,286 A | 4/1994 | Stack et al. |
| 5,330,500 A | 7/1994 | Song |
| 5,342,348 A | 8/1994 | Kaplan |
| 5,342,621 A | 8/1994 | Eury |
| 5,356,433 A | 10/1994 | Rowland et al. |
| 5,383,928 A | 1/1995 | Scott et al. |
| 5,389,106 A | 2/1995 | Tower |
| 5,411,551 A | 5/1995 | Winston et al. |
| 5,413,597 A | 5/1995 | Krajicek |
| 5,419,760 A | 5/1995 | Narciso, Jr. |
| 5,421,955 A | 6/1995 | Lau et al. |
| 5,439,446 A | 8/1995 | Barry |
| 5,441,515 A | 8/1995 | Khosravi et al. |
| 5,458,605 A | 10/1995 | Klemm |
| 5,514,154 A | 5/1996 | Lau et al. |
| 5,527,337 A | 6/1996 | Stack et al. |
| 5,578,075 A | 11/1996 | Dayton |
| 5,605,696 A | 2/1997 | Eury et al. |
| 5,700,286 A | 12/1997 | Tartaglia et al. |
| 5,707,385 A | 1/1998 | Williams |
| 5,780,807 A | 7/1998 | Saunders |
| 5,830,217 A | 11/1998 | Ryan |
| 5,843,172 A | 12/1998 | Yan |
| 6,131,266 A | 10/2000 | Saunders |
| 6,146,322 A | 11/2000 | Papirov et al. |
| 6,152,869 A | 11/2000 | Park et al. |
| 6,168,602 B1 | 1/2001 | Ryan |
| 6,254,632 B1 | 7/2001 | Wu et al. |
| 6,261,316 B1 | 7/2001 | Shaolian et al. |
| 6,261,320 B1 | 7/2001 | Tam et al. |
| 6,273,908 B1 | 8/2001 | Ndondo-Lay |
| 6,379,381 B1 | 4/2002 | Hosainy et al. |
| 6,391,033 B2 | 5/2002 | Ryan |
| 6,419,692 B1 | 7/2002 | Yang et al. |
| 6,432,133 B1 | 8/2002 | Lau et al. |
| 6,436,132 B1 | 8/2002 | Patel et al. |
| 6,530,950 B1 | 3/2003 | Alvarado et al. |
| 6,540,776 B2 | 4/2003 | Sanders Millare et al. |
| 6,613,084 B2 | 9/2003 | Yang |
| 6,629,992 B2 | 10/2003 | Bigus et al. |
| 6,629,994 B2 | 10/2003 | Gomez et al. |
| 6,663,665 B2 | 12/2003 | Shaolian et al. |
| 6,899,727 B2 | 5/2005 | Armstrong et al. |
| 6,939,368 B2 | 9/2005 | Simso |
| 2002/0138129 A1 | 9/2002 | Armstrong et al. |
| 2003/0078647 A1 | 4/2003 | Vallana et al. |
| 2003/0114919 A1 | 6/2003 | McQuiston et al. |
| 2003/0153901 A1* | 8/2003 | Herweck et al. ............ 604/891.1 |
| 2003/0166779 A1 | 9/2003 | Khemani et al. |
| 2003/0181973 A1 | 9/2003 | Sahota |
| 2003/0212447 A1 | 11/2003 | Euteneuer et al. |

FOREIGN PATENT DOCUMENTS

| | | |
|---|---|---|
| DE | 44 07 079 | 9/1994 |
| EP | 0 567 788 | 11/1993 |
| EP | 0 604 022 | 1/1994 |
| EP | 0 578 998 | 6/1994 |
| EP | 0 621 017 | 10/1994 |
| EP | 0 623 354 | 11/1994 |
| WO | WO 91/17789 | 11/1991 |
| WO | WO 93/06792 | 4/1993 |
| WO | WO 95/29647 | 11/1995 |

OTHER PUBLICATIONS

Casper et al., "Fiber-Reinforced Absorbable Composite for Orthopedic Surgery", Science and Engineering, vol. 53, pp. 497-501, Fall Meeting 1985.

Hahn et al., "Glow Discharge Polymers as Coatings for Implanted Devices", Univ. of Missouri, pp. 109-113, 1981.

Hahn et al., "Biocompatibility of Glow-Discharge-Polymerized Films and Vacuum-Deposited Parylene", Applied Polymer Symposium 38, pp. 55-64, 1984.

Kelley et al., "Totally Resorbable High-Strength Composite Material", Advances in Biomedical Polymers, Ed. By Charles G. Gebelein, pp. 75-85, 1987.

Muller et al., "Advances in Coronary Angioplasty: Endovascular Stents", Coronary Artery Disease, vol. 1, No. 4, 10 pgs, 1990.

Nichols et al., "Electrical Insulation of Implantable Devices by Composite Polymer Coatings", Univ. of Missouri, Paper No. 87-0110, pp. 57-62, 1987.

Olson "Parylene, a Biostable Coating for Medical Applications", Nova Tran Parylene Coating Services Jul. 25, 1988 and Nov. 14, 1988 10 pgs.

"Parylene Conformal Coating" by Nova Tran Custom Coating Services, 8 pgs, (undated).

Schatz "A View of Vascular Stents", Arizona Heart Institute Foundation, Phoenix Arizona, 15 pgs, 1988.

Schmidt et al., "Long-Term Implants of Parylene-C Coated Microelectrodes", Medical & Biological Engineering & Computing, pp. 96-101, 1988.

Shing-Chiu Wong et al., "An Update on Coronary Stents", Cardio, Feb. 1992, 8 pgs.

* cited by examiner

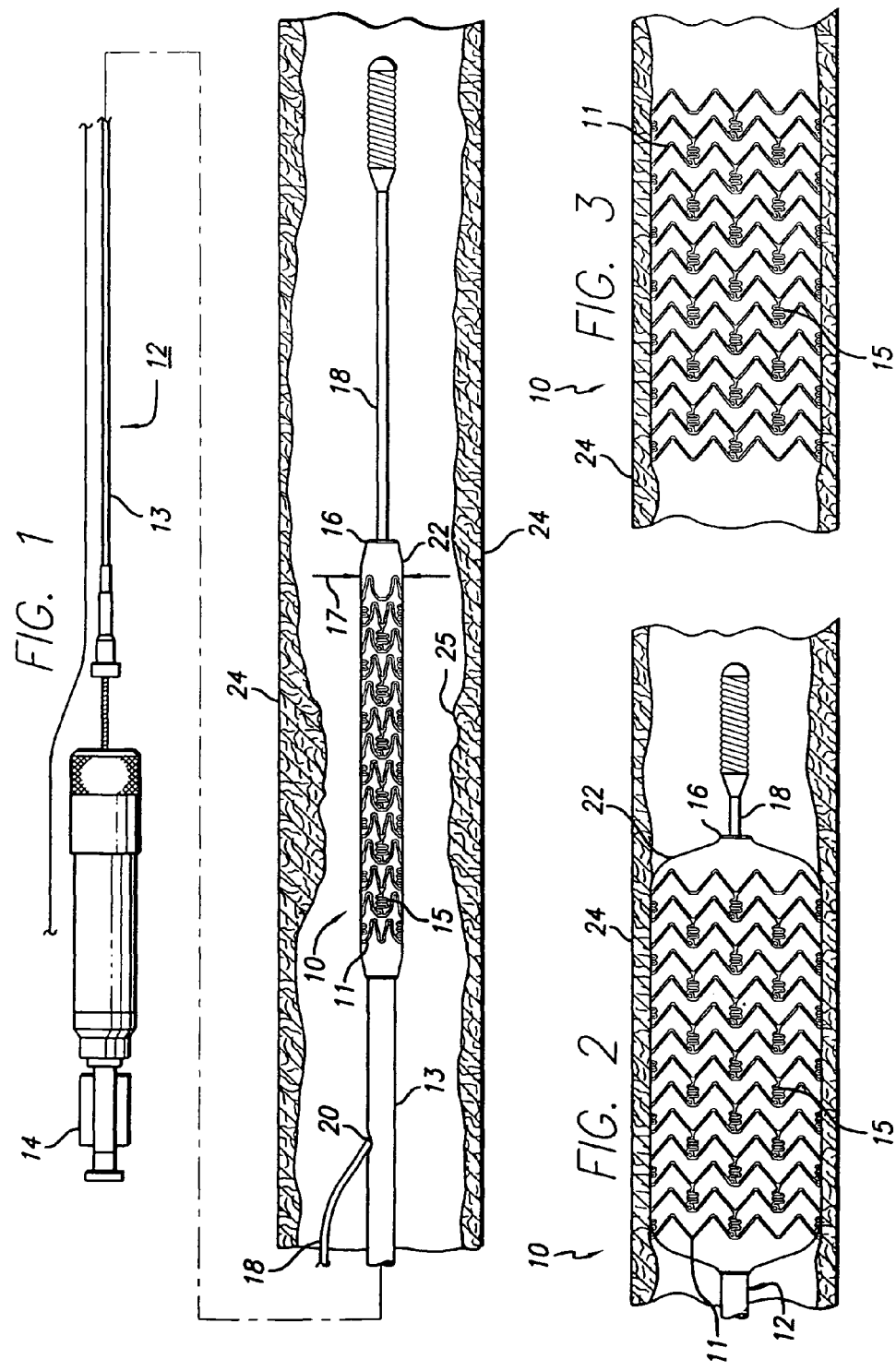

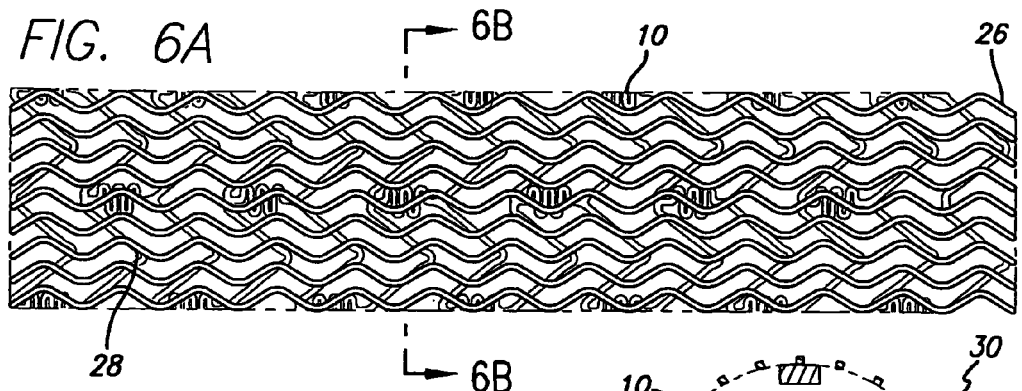
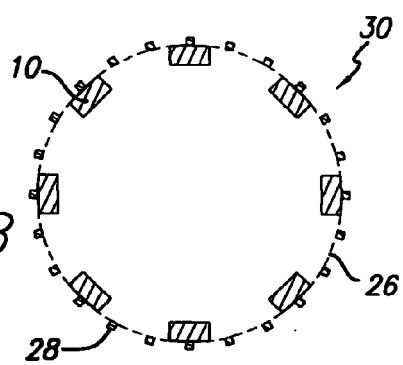
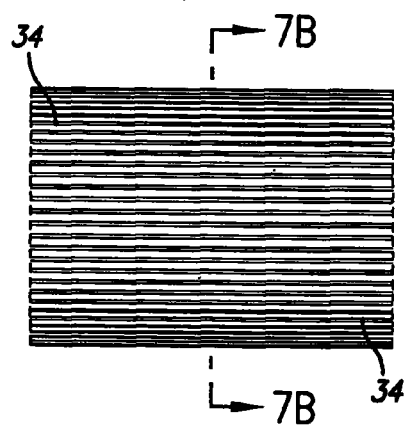
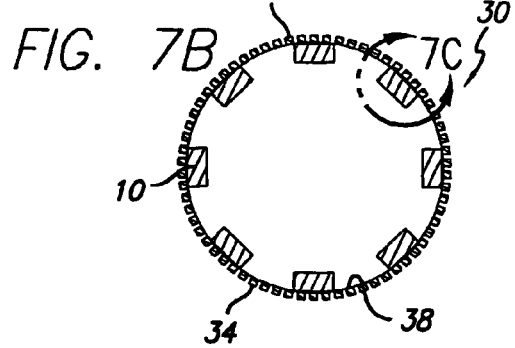
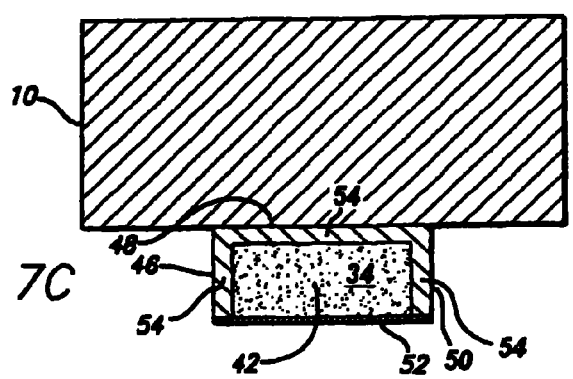

DRUG-ELUTING STENT WITH FILAMENT STRANDS

CROSS REFERENCE TO RELATED APPLICATIONS

This is a divisional application of U.S. patent application Ser. No. 10/293,108, filed on Nov. 13, 2002 now U.S. Pat. No. 7,144,422.

BACKGROUND OF THE INVENTION

This invention relates to vascular repair devices, and in particular intravascular stents, which are adapted to be implanted into a patient's body lumen, such as a blood vessel or coronary artery, to maintain the patency thereof. Stents are particularly useful in the treatment of atherosclerotic stenosis in arteries and blood vessels. More particularly, the invention concerns a drug-eluting stent delivery system consisting of an intravascular device having a local drug-eluting component that is capable of eluting therapeutic drugs with uniform and controlled drug distribution at the treatment site while providing the intravascular device with a biocompatible and/or hemocompatible surface.

Intravascular interventional devices such as stents are typically implanted within a vessel in a contracted state, and expanded when in place in the vessel in order to maintain the patency of the vessel to allow fluid flow through the vessel. Stents have a support structure such as a metallic structure to provide the strength required to maintain the patency of the vessel in which it is to be implanted, and are typically provided with an exterior surface coating to provide a biocompatible and/or hemocompatible surface. Since it is often useful to provide localized therapeutic pharmacological treatment of a blood vessel at the location being treated with the stent, it is also desirable to provide intravascular interventional devices such as stents with a biocompatible and/or hemocompatible surface coating of a polymeric material with the capability of being loaded with therapeutic agents, to function together with the intravascular devices for placement and release of the therapeutic drugs at a specific intravascular site.

Drug-eluting stent devices have shown great promise in treating coronary artery disease, specifically in terms of reopening and restoring blood flow in arteries stenosed by atherosclerosis. Restenosis rates after using drug-eluting stents during percutaneous intervention are significantly lower compared to bare metal stenting and balloon angioplasty. However, current design and fabrication methods for drug-eluting stent devices are not optimal. Accordingly, various limitations exist with respect to such current design and fabrication methods for drug-eluting stents.

One significant limitation, for example, is that current designs for drug-eluting stents fail to provide for uniform drug distribution in the artery. Since uniformity is dictated by metal stent skeletal structure, increasing uniformity by increasing the metal stent surface area makes the stent stiff and compromises flexibility and deliverability. Additionally, current device designs incorporate expandable ring elements and connectors, which are then coated using a polymer plus drug coating or loaded with microreservoirs of drug. The expandable nature of the rings limits the extent of uniformity in coverage and drug distribution that can be achieved. Further limitations include the mixture of the drug in a polymer and/or solvent solution which is then spray coated on the entire stent surface with a primer, drug, and topcoat layers being used to control release kinetics. This approach tends to cause cracking in the drug-coating layer, since the layer also undergoes stretching during stent expansion, and considerable washout of the drug into the blood stream, and only a fraction gets into the tissue/artery. Further, the amount of the drug that can be loaded on the stent is limited by mechanical properties of the coating, since the higher the drug content in the polymer makes the coating more brittle and causes cracking thereto. Therefore, loading a higher drug dose requires coating with more polymer on the device. Other limitations in current fabrication methods of drug-eluting stents include the necessity of several coating steps along the length of the stent which is time consuming. Special equipment for crimping the drug-eluting stent on the balloon and to securely attach the stent on the balloon is also needed in accordance with current fabrication methods. As conventional spray coating is capable of programming only one drug release rate kinetics, variation of drug dosing and release kinetics along the length of the stent is not possible using the current coating process.

What has been needed and heretofore unavailable is a novel design that decouples the two major functional characteristics of the drug-eluting stent device, namely the purely mechanical stent structure and the local drug-eluting component. Current devices are constrained by their design construct which necessitates optimizing both factors—mechanical stent expansion and drug-elution kinetics simultaneously. Thus, it would be desirable to have a stent structure that is optimally designed for expansion (i.e., allowable stress/strain, scaffolding, radial strength, etc.) independent of the drug-eluting component, and the drug-eluting component designed for local drug release independent of mechanical factors associated with stent expansion. The present invention meets these and other needs.

SUMMARY OF THE INVENTION

The present invention is directed to intraluminal devices, and more particularly, to a drug-eluting stent delivery system for controlled release of therapeutic drugs and for delivery of the therapeutic drugs in localized drug therapy in a blood vessel. Alternatively, the drug-eluting stent delivery system includes a plurality of individual filament strands attached in a spaced apart orientation around an outside surface area of the stent and loaded with at least one therapeutic drug for the controlled release thereof at a treatment site. Methods for making different types of a drug-eluting stent delivery system are also disclosed herein.

In one embodiment, the present invention accordingly provides for a drug-eluting stent delivery system for controlled release of therapeutic drugs and for delivery of the therapeutic drugs in localized drug therapy in a blood vessel. A pattern of struts are interconnected to form a structure that contacts the walls of a body lumen to maintain the patency of the vessel. The pattern of struts include a plurality of flexible cylindrical rings being expandable in a radial direction with each of the rings having a first delivery diameter and a second implanted diameter while aligned on a common longitudinal axis. At least one link of the stent is attached between adjacent rings to form the stent. The stent is formed at least in part of a metallic material such as stainless steel, platinum, titanium, tantalum, nickel-titanium, cobalt-chromium or alloys thereof.

A polymeric sleeve, fabricated as a prepatterned tube, is loaded with at least one therapeutic drug for the release thereof at a treatment site. The polymeric sleeve is attached to at least a portion of an outside surface area of the stent structure. Various therapeutic drugs that can be used in combination with the polymeric sleeve include antiplatelets, anticoagulants, antifibrins, antiinflammatories, antithrombins, and antiproliferatives. Several drug-loadable polymers, such as PMMA, EVAL, PBMA, PGA, PLLA, copolymers and blends thereof and nanotubes of carbon can be used to fabricate the drug-loaded sleeve of the invention. The thickness of the drug-loaded polymeric sleeve ranges from about 0.001 to about 100 microns.

The polymeric sleeve is fabricated from a predesigned pattern having individual drug-loaded elements to form a desired local drug-elution profile. The predesigned pattern of the polymeric sleeve as a solid tube can be formed by various techniques such as etching or cutting. The drug-loaded polymeric sleeve is prefabricated in a desired dimension by using one of the known polymer processing techniques in the art including extrusion, injection molding, laser cutting, slip casting, and plasma polymerization. As a further mechanism of controlling elution of the therapeutic drug at the treatment site, the polymeric sleeve can be coated with at least one additional layer of polymer material as a barrier layer.

In use, the drug-loaded polymeric sleeve breaks away in the predesigned pattern upon expansion of the underlying stent structure and individual drug-loaded elements are held against the vessel wall by the stent structure. The predesigned pattern is fabricated to expand along a length of the stent to overcome strain.

In another embodiment, the present invention provides for a drug-eluting stent delivery system for controlled release of therapeutic drugs and for delivery of the therapeutic drugs in localized drug therapy in a blood vessel. A pattern of struts are interconnected to form a first stent structure that contacts the walls of a body lumen to maintain the patency of the vessel, wherein a second stent structure, fabricated as a prepatterned thin metallic sheet having a polymer layer disposed thereon, is loaded with at least one therapeutic drug for the release thereof at a treatment site. The second stent structure is attached to at least a portion of an outside surface area of the stent structure. The second stent structure is not limited to a tubular form and can be wrapped around the first stent structure in a jelly roll configuration.

In a further embodiment, the present invention provides for a drug-eluting stent delivery system for controlled release of therapeutic drugs and for delivery of the therapeutic drugs in localized drug therapy in a blood vessel. A pattern of struts are interconnected to form a structure that contacts the walls of the body lumen to maintain the patency of the vessel. A plurality of individual filament strands are attached to an outside surface of the stent structure in a spaced apart orientation and loaded with at least one therapeutic drug for the release thereof at a treatment site. The plurality of individual filament strands are positioned longitudinally across the outside surface of the stent structure.

The pattern of struts include a plurality of flexible cylindrical rings being expandable in a radial direction, each of the rings having a first delivery diameter and a second implanted diameter while aligned on a common longitudinal axis. At least one link of the stent is attached between adjacent rings to form the stent. The stent is formed at least in part of a metallic material such as stainless steel, platinum, titanium, tantalum, nickel-titanium, cobalt-chromium, and alloys thereof.

Various therapeutic drugs can be used in combination with the drug-eluting stent delivery system of the present invention including antiplatelets, anticoagulants, antifibrins, antiinflammatories, antithrombins, and antiproliferatives. The plurality of individual filament strands can be fabricated using different therapeutic drug combinations for the release thereof at the treatment site. The drug-loaded filament strands each have a thickness in the range of about 0.001 to about 100 microns and a width in the range of about 0.001 to about 50 microns. Several drug-loadable polymers, such as PMMA, EVAL, PBMA, PGA, PLLA, copolymers and blends thereof, and nanotubes of carbon can be used to fabricate the individual filament strands. Alternatively, the plurality of individual filament strands are fabricated from a porous metal having a polymeric drug release layer disposed thereon.

Each of the individual filament strands has a rectangular cross-section with a first side, a second side, a third side, and a fourth side. A barrier coating layer is disposed on the first, second, and third sides of each of the drug-loaded filament strands to enable drug elution along the fourth side at the treatment site. Alternatively, the plurality of individual filament strands can be configured to assume a different cross-sectional design such as circular, oval, triangular, trapezoidal, and tubular designs. The individual filament strands can be fabricated from either a micron-scale level or a nano-scale level to form microfilament strands or nanofilament strands, respectively.

In another embodiment, the present invention provides for a drug-eluting stent delivery system for controlled release of therapeutic drugs and for delivery of the therapeutic drugs in localized drug therapy in a blood vessel. A pattern of struts are interconnected to form a structure that contacts the walls of a body lumen to maintain the patency of the vessel. A polymeric sleeve, fabricated as a prepatterned tube, is loaded with at least one therapeutic drug for the release thereof at a treatment site, the polymeric sleeve being attached to at least a portion of an inside surface area of the stent structure for the treatment of the inner arterial region of the vessel.

In yet another embodiment, the present invention provides for a method of making a drug-eluting stent delivery system for controlled release of therapeutic drugs and for delivery of the therapeutic drugs in localized drug therapy in a blood vessel. The method includes providing a pattern of struts interconnected to form a structure that contacts the walls of a body lumen to maintain the patency of the vessel. A polymeric sleeve, fabricated as a prepatterned tube, is attached to at least a portion of an outside surface area of the stent structure. The polymeric sleeve is loaded with at least one therapeutic drug for the release thereof at a treatment site.

In a further embodiment, the present invention provides for a method of making a drug-eluting stent delivery system for controlled release of therapeutic drugs and for delivery of the therapeutic drugs in localized drug therapy in a blood vessel. The method includes providing a pattern of struts interconnected to form a structure that contacts the walls of the body lumen to maintain the patency of the vessel. A plurality of individual filament strands are positioned longitudinally across an outside surface of the stent structure in a spaced apart orientation and attached thereto. The plurality of individual filament strands are loaded with at least one therapeutic drug for the release thereof at a treatment site.

Other features and advantages of the invention will become apparent from the following detailed description, taken in conjunction with the accompanying drawings, which illustrate, by way of example, the features of the invention.

BRIEF DESCRIPTION OF THE DRAWINGS

FIG. 1 is an elevational view, partially in section, of a stent embodying features of the invention which is mounted on a delivery catheter and disposed within a damaged artery.

FIG. 2 is an elevational view, partially in section, similar to that shown in FIG. 1 wherein the stent is expanded within a damaged artery.

FIG. 3 is an elevational view, partially in section, depicting the expanded stent within the artery after withdrawal of the delivery catheter.

FIG. 6A is a plan view of the drug-eluting stent delivery system in accordance with the invention shown in the expanded condition.

FIG. 6B is a transverse, cross-sectional view of the drug-eluting stent delivery system of FIG. 6A shown in the expanded condition.

FIG. 7A is a plan view of an alternative embodiment of the invention in an expanded condition depicting a plurality of individual filament strands for holding the therapeutic drug prior to being released.

FIG. 7B is a transverse, cross-sectional view of the alternative embodiment depicting a stent with the plurality of individual filament strands attached thereto in the expanded condition.

FIG. 7C is an enlarged, transverse, cross-sectional view of a section shown in FIG. 7B in the expanded condition.

DETAILED DESCRIPTION OF THE PREFERRED EMBODIMENTS

Figure 4A:
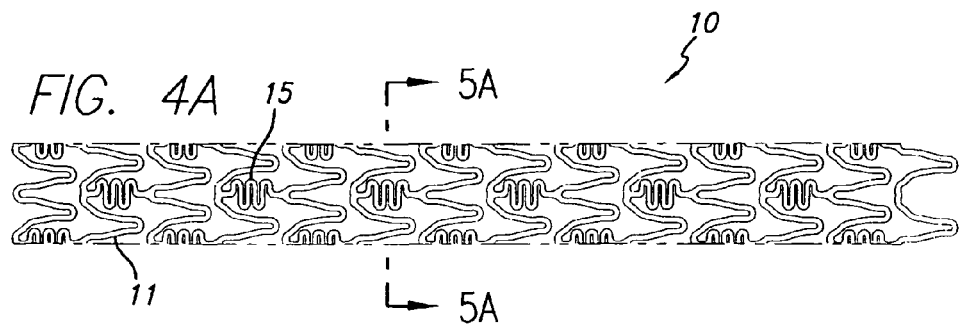
FIG. 4A is a plan view of a flattened stent of the invention which illustrates the pattern of the stent shown in FIGS. 1-3 in an unexpanded condition.

As shown in the drawings for purposes of illustration, the present invention is directed to a drug-eluting stent delivery system which includes a mechanical component and a local drug-eluting component, namely an intravascular stent and a prepatterned polymeric sleeve for controlled release of therapeutic drugs and for delivery of the therapeutic drugs in localized drug therapy in a blood vessel. The present invention is also directed to an intravascular stent having a drug-eluting component in the form of a plurality of microfilament strands attached to an outside surface of the stent structure in a spaced apart orientation. Methods of making a drug-eluting stent delivery system having a drug-eluting component disposed in the form of a prepatterned polymeric sleeve or a plurality of microfilament strands for controlled release and delivery of therapeutic drugs in localized drug therapy in a blood vessel are also disclosed herein.

Turning to the drawings, FIG. 1 depicts a metallic stent 10, incorporating features of the invention, mounted on a catheter assembly 12 which is used to deliver the stent and implant it in a body lumen, such as a coronary artery, carotid artery, peripheral artery, or other vessel or lumen within the body. The stent generally comprises a plurality of radially expandable cylindrical rings 11 disposed generally coaxially and interconnected by undulating links 15 disposed between adjacent cylindrical elements. The catheter assembly includes a catheter shaft 13 which has a proximal end 14 and a distal end 16. The catheter assembly is configured to advance through the patient's vascular system by advancing over a guide wire by any of the well known methods of an over the wire system (not shown) or a well known rapid exchange catheter system, such as the one shown in FIG. 1.

Catheter assembly 12 as depicted in FIG. 1 is of the well known rapid exchange type which includes an RX port 20 where the guide wire 18 will exit the catheter. The distal end of the guide wire 18 exits the catheter distal end 16 so that the port 20 and the catheter distal end 16. As is known in the art, the guide wire lumen which receives the guide wire is sized for receiving various diameter guide wires to suit a particular application. The stent is mounted on the expandable member 22 (balloon) and is crimped tightly thereon so that the stent and expandable member present a low profile diameter for delivery through the arteries.

As shown in FIG. 1, a partial cross-section of an artery 24 is shown with a small amount of plaque that has been previously treated by an angioplasty or other repair procedure. Stent 10 of the present invention is used to repair a diseased or damaged arterial wall which may include the plaque 25 as shown in FIG. 1, or a dissection, or a flap which are commonly found in the coronary arteries, carotid arteries, peripheral arteries and other vessels.

In a typical procedure to implant stent 10, the guide wire 18 is advanced through the patient's vascular system by well known methods so that the distal end of the guide wire is advanced past the plaque or diseased area 25. Prior to implanting the stent, the cardiologist may wish to perform an angioplasty procedure or other procedure (i.e., atherectomy) in order to open the vessel and remodel the diseased area. Thereafter, the stent delivery catheter assembly 12 is advanced over the guide wire so that the stent is positioned in the target area. The expandable member or balloon 22 is inflated by well known means so that it expands radially outwardly and in turn expands the stent radially outwardly until the stent is apposed to the vessel wall. The expandable member is then deflated and the catheter withdrawn from the patient's vascular system. The guide wire typically is left in the lumen for post-dilatation procedures, if any, and subsequently is withdrawn from the patient's vascular system. As depicted in FIGS. 2 and 3, the balloon is fully inflated with the stent expanded and pressed against the vessel wall, and in FIG. 3, the implanted stent remains in the vessel after the balloon has been deflated and the catheter assembly and guide wire have been withdrawn from the patient.

The stent 10 serves to hold open the artery 24 after the catheter is withdrawn, as illustrated by FIG. 3. Due to the formation of the stent from an elongated tubular member, the undulating components of the stent are relatively flat in transverse cross-section, so that when the stent is expanded, it is pressed into the wall of the artery and as a result does not interfere with the blood flow through the artery. The stent is pressed into the wall of the artery and will eventually be covered with endothelial cell growth which further minimizes blood flow interference. The undulating portion of the stent provides good tacking characteristics to prevent stent movement within the artery. Furthermore, the closely spaced cylindrical elements at regular intervals provide uniform support for the wall of the artery, and consequently are well adapted to tack up and hold in place small flaps or dissections in the wall of the artery, as illustrated in FIGS. 2 and 3.

The stent patterns shown in FIGS. 1-3 are for illustration purposes only and can vary in size and shape to accommodate different vessels or body lumens. Further, the metallic stent 10 is of a type that can be used in accordance with the present invention.

The drug-eluting stent delivery system of the present invention is applicable to all vascular stent applications in the body including coronary and peripheral arterial system. Further, the present invention can be used in the treatment of vulnerable plaque such as thin fibrous-capped atheromatic vulnerable lesions using desired drug and release kinetics with site specificity. In addition, the drug-eluting component of the stent system can be incorporated on all stent platforms for all sizes and lengths including a bifurcated stent structure to achieve uniform drug distribution along the entire vessel including the carina. It is also contemplated that the drug-eluting component of the present invention can be used for designing drug-eluting stent devices with thinner stent struts (i.e., thickness ranging between 5-100 microns) without compromising the structural integrity of the stent, deliverability and optimal drug elution.

The present invention overcomes all of the earlier mentioned limitations through a novel design that decouples the two major functional characteristics of the drug-eluting stent delivery system, namely the purely mechanical stent structure and the local drug-eluting component. Each component is independently designed and optimized for its functional characteristics and the optimal drug-eluting stent delivery system is conceived and assembled. The stent structure is optimally designed for expansion (i.e., allowable stress/strain, scaffolding, and radial strength), and the local drug-eluting component is optimally designed for controlled release of therapeutic drugs.

As shown in one embodiment, FIG. 4A is a plan view of a flattened stent of the drug-eluting stent delivery system which illustrates the pattern of the stent shown in FIGS. 1-3 in an unexpanded condition. The stent 10 is shown in a flattened condition so that the pattern can be clearly viewed, even though the stent is never in this form. The stent is typically formed from a tubular member, however, it can be formed from a flat sheet such as shown in FIG. 4A and rolled into a cylindrical configuration.

Figure 4B:
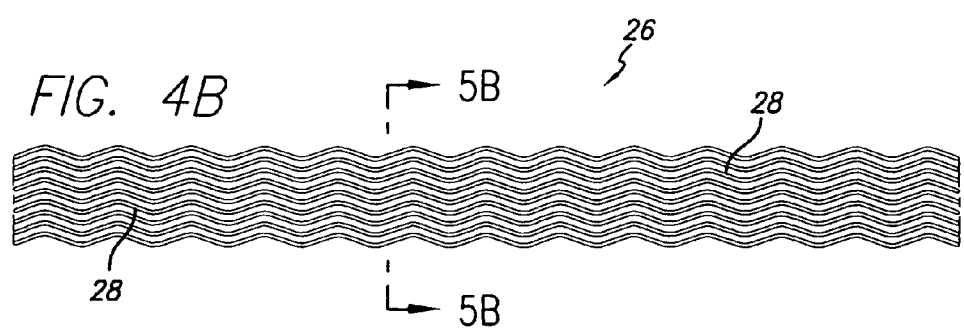
FIG. 4B is a plan view of a flattened drug-eluting component of the drug-eluting stent delivery system in accordance with the invention shown in the unexpanded condition.

FIG. 4B is a flattened, plan view of a prepatterned polymeric sleeve 26 of the stent 10 in accordance with the invention shown in the unexpanded condition. In this embodiment, the stent having a polymeric sleeve for controlled release of therapeutic drugs and for delivery of the therapeutic drugs in localized drug therapy in a blood vessel includes a pattern of struts interconnected to form a structure that contacts the walls of a body lumen to maintain the patency of the vessel. The pattern of struts include a plurality of flexible cylindrical rings 11 (FIG. 4A) being expandable in a radial direction, each of the rings having a first delivery diameter and a second implanted diameter and being aligned on a common longitudinal axis 17. At least one link 15 (FIG. 4A) of the stent is attached between adjacent rings to form the stent.

With further reference to FIG. 4B, the drug-eluting polymeric sleeve 26 is prefabricated in the desired dimensions using conventional polymer processing methods known in the art, including extrusion, injection molding, slip casting or plasma polymerization using a mixture of the polymer, solvent and drug in liquid, semi-solid or solid form. The polymeric sleeve can be fabricated either as a prepatterned tube or a solid tube. When the polymeric sleeve is fabricated as a solid tube, the predesigned pattern can be attained by the known methods in the art consisting of laser cutting or etching using the excimer or the avia solid-state laser without any post processing. The polymeric sleeve is fabricated from a predesigned pattern having individual drug-loaded elements 28 to form a desired local drug-elution profile. The intent of the predesigned pattern on the polymeric sleeve is to enable the detachment of the drug-eluting polymer elements upon stent expansion (FIG. 6A) without undergoing stretching during balloon expansion of the stent 10 and achieve an optimally desired drug-elution profile. Accordingly, upon stent expansion, the drug-loaded polymeric sleeve breaks away in the predesigned pattern and individual drug-loaded elements are held against the vessel wall (not shown) by the stent structure 10. The predesigned pattern can be fabricated so that it expands along a length of the stent if needed to overcome strain during expansion. Depending on the desired nature of local drug elution and drug uptake into the artery, a variety of different patterns can be etched or cut into the polymeric material that forms the sleeve. The sleeve is attached to the stent using conventional metal-polymer or polymer-polymer adhesion techniques known in the art. The drug-loaded polymeric sleeve has a thickness in the range of about 0.001 to about 100 microns.

Figure 4C:
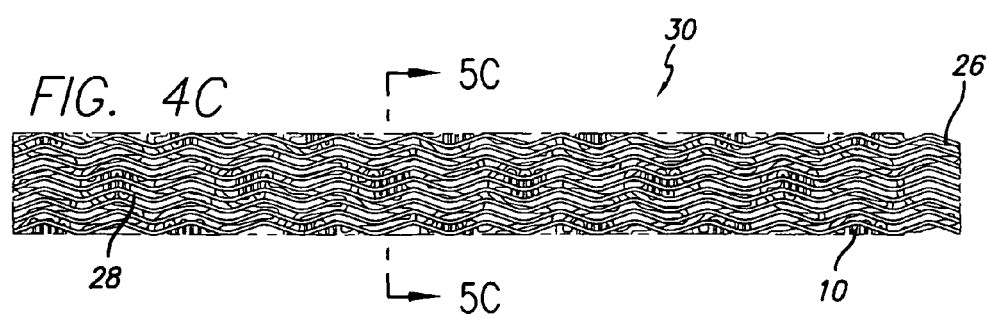
FIG. 4C is a plan view of the drug-eluting stent delivery system in accordance with the invention shown in the unexpanded condition.

FIG. 4C is a plan view of the drug-eluting stent delivery system 30 which includes a stent 10 with the drug-eluting component or polymeric sleeve 26 disposed thereon in accordance with the invention shown in the unexpanded condition.

Figure 5A:
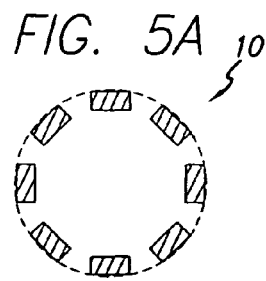
FIG. 5A is a transverse, cross-sectional view of the drug-eluting stent delivery system shown in FIG. 4A in the unexpanded condition.
Figure 5B:
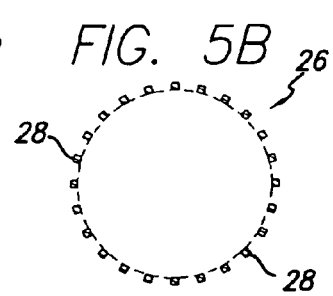
FIG. 5B is a transverse, cross-sectional view of the drug-eluting component of the drug-eluting stent delivery system shown in FIG. 4B in the unexpanded condition.
Figure 5C:
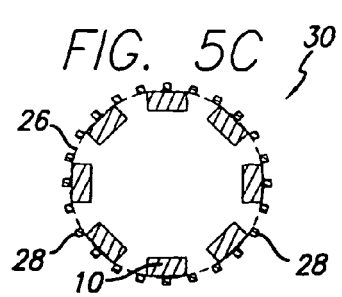
FIG. 5C is a transverse, cross-sectional view of the drug-eluting stent delivery system shown in FIG. 4C in the unexpanded condition.

FIGS. 5A-C depict various transverse, cross-sectional views of the two separate components of the drug-eluting stent delivery system 30, namely the mechanical stent structure 10 and the drug-eluting component or drug-loaded polymeric sleeve 26, and one of the complete present invention drug-eluting stent delivery system while in an unexpanded condition. More specifically, FIG. 5A is a transverse, cross-sectional view of the stent in FIG. 4A shown in the unexpanded condition. FIG. 5B is a transverse, cross-sectional view of the drug-eluting component of the stent in FIG. 4B shown in the unexpanded condition. FIG. 5C is a transverse, cross-sectional view of the stent with the drug-eluting component disposed thereon in FIG. 4C shown in the unexpanded condition.

FIG. 6A illustrates a plan view of the stent 10 with the drug-loaded polymeric sleeve 26 disposed thereon in accordance with the invention shown in the expanded condition. The present invention contemplates that the drug-loaded polymeric sleeve can have at least one additional layer of polymer material as a barrier layer to control elution of the therapeutic drug at the treatment site. Multiple layers of polymer material disposed on the polymeric sleeve provide further control of the elution of the therapeutic drug at the treatment site. It should be further recognized that the polymeric sleeve can optionally include multiple layers of the therapeutic drug disposed thereon. Accordingly, each of the layers of therapeutic drug can comprise a different therapeutic drug with varying release rates or a mixture of different therapeutic drugs. The outermost layer has a polymeric barrier coat layer to further control elution of the therapeutic drug. FIG. 6B illustrates a transverse, cross-sectional view of the drug-eluting stent delivery system 30 of FIG. 6A in the expanded condition. In this embodiment, the complete polymeric sleeve is also coated with a top coat or barrier layer (not shown) along the inner surface to prevent washout of the drug and increase efficiency of drug uptake into the artery.

In an alternative embodiment, the present invention provides for a drug-eluting stent delivery system for controlled release of therapeutic drugs and for delivery of the therapeutic drugs in localized drug therapy in a blood vessel. A pattern of struts are interconnected to form a first stent structure that contacts the walls of a body lumen to maintain the patency of the vessel. A second stent structure, fabricated as a prepatterned thin metallic sheet having a polymer layer disposed thereon, is loaded with at least one therapeutic drug for the release thereof at a treatment site, the second stent structure being attached to at least a portion of an outside surface area of the first stent structure. It should be appreciated that the second stent structure is not limited to a tubular form, and can be fabricated as a thin metallic sheet attached to the outside surface area of the first stent structure by being wrapped around the first stent structure in a jelly roll configuration. Various mechanisms for attaching the second stent structure to the outside surface area of the first stent structure are known in the art and contemplated for use with the present invention. Examples of such mechanisms for attachment include metal-polymer and polymer-polymer bonding technologies, such as by adhesives and other similar methods.

In another embodiment shown in FIGS. 7A-C, the present invention accordingly provides for a drug-eluting stent delivery system 30 having a drug-eluting component 34 for controlled release of therapeutic drugs and for delivery of the therapeutic drugs in localized drug therapy in a blood vessel. A pattern of struts are interconnected to form a structure 10 that contacts the walls of the body lumen to maintain the patency of the vessel. The pattern of struts include a plurality of flexible cylindrical rings 11 being expandable in a radial direction, each of the rings having a first delivery diameter and a second implanted diameter and being aligned on a common longitudinal axis 17. At least one link 15 of the stent is attached between adjacent rings to form the stent. A plurality of individual filament strands 34 are attached to an outside surface 38 of the stent structure in a spaced apart orientation, wherein the plurality of filament strands are each loaded with at least one therapeutic drug 42 for the release thereof at a treatment site. The plurality of individual filament strands are each positioned longitudinally across the outside surface of the stent structure.

FIG. 7A illustrates a typical arrangement of the individual filament strands 34 prior to their attachment to an outside surface of the stent structure in a spaced apart orientation. The filament strands are pre-loaded with at least one therapeutic drug for the eventual release thereof at the treatment site. It should be appreciated that the present invention contemplates the use of several different types of therapeutic drugs and drug cocktail combinations by incorporating different filament strands fabricated using different therapeutic drugs and therapeutic drugs with polymers for the eventual release thereof at the treatment site. The drug-loaded filament strands have dimensions of about 0.001 to about 100 microns in thickness and about 0.001 to about 50 microns in width. These filament strands can be fabricated from the micron to nanoscale level as wires or tubes from polymers and metals.

FIG. 7B is a transverse, cross-sectional view of the alternative embodiment of the invention, depicting a stent 10 with the plurality of individual filaments 34 attached thereto in the expanded condition. The plurality of individual filaments can be attached to the outside surface 38 of the stent by utilizing one of the techniques known in the art including metal-polymer and polymer-polymer bonding technologies (i.e., adhesives). The drug-loaded filaments can be designed to expand along the length of the stent to overcome strain as a result of expansion if necessary.

Referring to FIG. 7C, each individual drug-loaded filament strand 34 has a rectangular cross section 44 with a first side 46, second side 48, third side 50, and a fourth side 52. A polymeric barrier coating layer 54 is disposed on the first through third sides of each of the drug-loaded filament strands to enable drug elution along the fourth side at the treatment site. This layered construct increases the efficiency of drug transfer into the artery with minimal washout of the therapeutic drug. Accordingly, a lesser amount of drug 42 and less polymer are needed to deliver the appropriate therapeutic dose of drug into the artery. The local drug release rate at specific sites along the length and diameter of the stent can be varied by incorporating filament strands with different drug release rates into the drug-eluting stent delivery system. Further, the drug-loaded filament strands can have multiple layers of polymer to control drug elution kinetics, such as a top coat barrier layer to control or prevent drug release. Optionally, each filament strand can comprise multiple layers for loading with different therapeutic drugs or a mixture of different therapeutic drugs. The outermost layer has a polymeric barrier coat layer to further control elution of the therapeutic drug.

Other cross sectional designs may be utilized and optimized to achieve the desired drug elution kinetics of the present invention. Examples of alternative cross sectional designs that may be employed for use with the drug-eluting stent delivery system include circular, oval, triangular, trapezoidal, and tubular designs. The plurality of individual filament strands can be alternatively fabricated from a porous metal having a polymeric drug release layer disposed thereon.

It should be appreciated that the drug-loaded filament strands 34 can be used in combination with the polymeric sleeve 26 embodiment. In such an arrangement, each individual drug-loaded filament strand is placed longitudinally along the outside surface of the polymeric sleeve and attached thereto by polymer-polymer bonding or other similar methods (i.e. adhesives) known in the art. A barrier coating layer 54 is disposed on the first through third sides of each of the drug-loaded filament strands to enable drug elution along the fourth side at the treatment site as shown in FIG. 7C.

Alternatively, the present invention provides for a drug-eluting stent delivery system for controlled release of therapeutic drugs and for delivery of the therapeutic drugs in localized drug therapy in a blood vessel. A pattern of struts are interconnected to form a structure that contacts the walls of a body lumen to maintain the patency of the vessel, wherein a polymeric sleeve, fabricated as a prepatterned tube, is loaded with at least one therapeutic drug for the release thereof at a treatment site. The polymeric sleeve can be attached to at least a portion of an inside surface area of the stent structure to provide for appropriate treatment of the inner arterial region through release of the therapeutic drug in that region of the vessel where the stent is placed.

Examples of various metals or alloys used in forming the mechanical stent structure of the present invention drug-eluting stent delivery system include stainless steel, platinum, titanium, tantalum, nickel-titanium, cobalt-chromium, and alloys thereof. The stent can also be formed of a polymeric material such as PMMA, PGA or PLLA. Examples of various polymers used in forming the local drug-eluting component of the drug-eluting stent delivery system for all of the embodiments include PMMA, EVAL, PBMA, biodegradable polymers (i.e., PGA and PLLA), copolymers and blends thereof, and nanotubes of carbon. As set forth above, the local drug-eluting component may be alternatively fabricated from various metals or alloys, including stainless steel, platinum, titanium, tantalum, nickel-titanium, cobalt-chromium, and alloys thereof.

Examples of therapeutic drugs or pharmacologic compounds that may be loaded into the prefabricated patterned, polymeric sleeve or individual filament strands and delivered to the target site in the vasculature include taxol, aspirin, prostaglandins, and the like. Various therapeutic agents such as antithrombogenic or antiproliferative drugs are used to further control local thrombosis. Examples of therapeutic agents or drugs that are suitable for use in accordance with the present invention include sirolimus, everolimus, actinomycin D (ActD), taxol, paclitaxel, or derivatives and analogs thereof. Examples of agents include other antiproliferative substances as well as antineoplastic, antiinflammatory, antiplatelet, anticoagulant, antifibrin, antithrombin, antimitotic, antibiotic, and antioxidant substances. Examples of antineoplastics include taxol (paclitaxel and docetaxel). Further examples of therapeutic drugs or agents include antiplatelets, anticoagulants, antifibrins, antiinflammatories, antithrombins, and antiproliferatives. Examples of antiplatelets, anticoagulants, antifibrins, and antithrombins include, but are not limited to, sodium heparin, low molecular weight heparin, hirudin, argatroban, forskolin, vapiprost, prostacyclin and prostacyclin analogs, dextran, D-phe-pro-arg-chloromethylketone (synthetic antithrombin), dipyridamole, glycoprotein IIb/IIIa platelet membrane receptor antagonist, recombinant hirudin, thrombin inhibitor (available from Biogen located in Cambridge, Mass.), and 7E-3B® (an antiplatelet drug from Centocor located in Malvern, Pa.). Examples of antimitotic agents include methotrexate, azathioprine, vincristine, vinblastine, fluorouracil, adriamycin, and mutamycin. Examples of cytostatic or antiproliferative agents include angiopeptin (a somatostatin analog from Ibsen located in the United Kingdom), angiotensin converting enzyme inhibitors such as Captopril® (available from Squibb located in New York, N.Y.), Cilazapril® (available from Hoffman-LaRoche located in Basel, Switzerland), or Lisinopril® (available from Merck located in Whitehouse Station, N.J.); calcium channel blockers (such as Nifedipine), colchicine, fibroblast growth factor (FGF) antagonists, fish oil (omega 3-fatty acid), histamine antagonists, Lovastatin® (an inhibitor of HMG-CoA reductase, a cholesterol lowering drug from Merck), methotrexate, monoclonal antibodies (such as PDGF receptors), nitroprusside, phosphodiesterase inhibitors, prostaglandin inhibitor (available from GlaxoSmithKline located in United Kingdom), Seramin (a PDGF antagonist), serotonin blockers, steroids, thioprotease inhibitors, triazolopyrimidine (a PDGF antagonist), and nitric oxide. Other therapeutic drugs or agents which may be appropriate include alpha-interferon, genetically engineered epithelial cells, and dexamethasone.

While the foregoing therapeutic agents have been used to prevent or treat restenosis, they are provided by way of example and are not meant to be limiting, since other therapeutic drugs may be developed which are equally applicable for use with the present invention. The treatment of diseases using the above therapeutic agents is known in the art. The calculation of dosages, dosage rates and appropriate duration of treatment are previously known in the art. Furthermore, the therapeutic drugs or agents are loaded at desired concentration levels per methods well known in the art to render the device ready for implantation.

In use, the stent is deployed using conventional techniques. Once in position, the therapeutic drug gradually diffuses into adjacent tissue at a rate dictated by the parameters associated with the polymer coat layer. The total dosage that is delivered is of course limited by the total amount of the therapeutic drug that had been loaded within the polymer sleeve or within each individual strand of the plurality of microfilaments. The therapeutic drug is selected to treat the deployment site and/or locations downstream thereof. For example, deployment in the carotid artery will serve to deliver such therapeutic drug to the brain.

The present invention also provides for various methods of making a drug-eluting stent delivery system 30 for controlled release of therapeutic drugs and for delivery of the therapeutic drugs in localized drug therapy in a blood vessel. In one embodiment, the method includes providing a pattern of struts interconnected to form a structure 10 that contacts the walls of a body lumen to maintain the patency of the vessel. A polymeric sleeve 26, fabricated as a prepatterned tube, is attached to at least a portion of an outside surface area 38 of the stent structure. Fabrication of the polymeric sleeve may be accomplished through using a variety of different techniques known in the art which include extrusion, laser cutting, plasma polymerization, slip casting, injection molding and similar techniques. The pattern of the polymeric tube may assume any desirable pattern which works to achieve an appropriate local drug-elution profile.

In an alternative embodiment, the local drug-eluting component 34 includes a plurality of individual filament strands which are longitudinally positioned across an outside surface 38 of a stent structure 10 in a spaced apart orientation and attached thereto. The plurality of individual filament strands are loaded with at least one therapeutic drug 42 for the release thereof at a treatment site.

The drug-loaded, polymeric sleeve 26 or the drug-loaded individual microfilament strands 34 can be processed directly by methods known in the art, such as by extrusion or plasma polymerization. The drug-loaded, prepatterned polymeric sleeve or the individual drug-loaded filament strands are preferably attached to the stent structure in the final stages of fabricating the drug-eluting stent delivery system, after the stent is crimped and securely attached to the balloon using current technology. The polymeric sleeves or filament strands of appropriate length are attached to the outer surface of the stent on the delivery system using various metal-polymer and polymer-polymer bonding technologies, such as adhesives.

The aforedescribed illustrative stent 10 of the present invention and similar stent structures can be made in many ways. One method of making the stent rings 11 is to cut a thin-walled tubular member, such as stainless steel tubing to remove portions of the tubing in the desired pattern for the stent, leaving relatively untouched the portions of the metallic tubing which are to form the rings. In accordance with the invention, it is preferred to cut the tubing in the desired pattern using a machine-controlled laser which process is well known in the art.

After laser cutting, the stent rings are preferably electrochemically polished in an acidic aqueous solution such as a solution of ELECTRO-GLO #300, sold by the ELECTRO-GLO Co., Inc. in Chicago, Ill., which is a mixture of sulfuric acid, carboxylic acids, phosphates, corrosion inhibitors and a biodegradable surface active agent. The bath temperature is maintained at about 110-135° F. and the current density is about 0.4 to about 1.5 amps per square inch. Cathode to anode area should be at least about two to one.

The foregoing laser cutting process to form the cylindrical rings 11 can be used with metals other than stainless steel including cobalt-chromium, titanium, tantalum, platinum, nickel-titanium, and alloys thereof, and other biocompatible metals suitable for use in humans, and typically used for intravascular stents. Further, while the formation of the cylindrical rings is described in detail, other processes of forming the rings are possible and are known in the art, such as by using chemical etching, electronic discharge machining, stamping, and other processes.

While the invention has been illustrated and described herein, in terms of its use as an intravascular stent, it will be apparent to those skilled in the art that the stent can be used in other body lumens. Further, particular sizes and dimensions, materials used, and the like have been described herein and are provided as examples only. Likewise, the invention is not limited to any particular method of forming the underlying medical device structure. Other modifications and improvements may be made without departing from the scope of the invention. Accordingly, it is not intended that the invention be limited, except as by the appended claims.

What is claimed is:

1. A stent for delivery of a drug in a body lumen, comprising:
   a plurality of interconnected struts forming a hollow structure having an interior passageway, the hollow structure including an inner surface facing the interior passageway and an outer surface opposite the inner surface and facing away from the interior passageway; and
   a plurality of drug-loaded filament strands attached to the outer surface, each drug-loaded filament strand having a rectangular cross section with a first side, a second side, a third side, and a fourth side, wherein a barrier coating layer is disposed on the first, second and third sides and not disposed on the fourth side to enable drug elution along the fourth side.

2. The stent of claim 1, wherein the drug-loaded filament strands are oriented substantially parallel to each other and distributed in a spaced apart configuration completely around the outer surface of the hollow structure.

3. The stent of claim 1, wherein the drug-loaded filament strands are attached exclusively to the outer surface.

4. The stent of claim 1, wherein the hollow structure is capable of expanding and the drug-loaded filament strands are capable of moving apart from each other when the hollow structure expands.

5. A stent for delivery of a drug in a body lumen, comprising:
   a plurality of interconnected struts forming a hollow structure having an interior passageway, the hollow structure including an inner surface facing the interior passageway and an outer surface opposite the inner surface and facing away from the interior passageway; and
   a plurality of drug-loaded filament strands, each filament strand attached to the outer surface and including a barrier layer configured to control elution of drug from filament strand,
   wherein each filament strand includes multiple layers of polymer, the outermost layer among the multiple layers being the barrier layer, and at least one layer of the multiple layers contains a drug.

6. The stent of claim of claim 5, wherein the plurality of drug-loaded filament strands are not woven about the plurality of interconnected struts.

7. The stent of claim 5, wherein the drug-loaded filament strands are oriented substantially parallel to each other and distributed in a spaced apart configuration completely around the outer surface of the hollow structure.

8. The stent of claim 5, wherein the drug-loaded filament strands are attached exclusively to the outer surface.

* * * * *